United States Patent [19]

Bryant

[11] 4,228,094

[45] Oct. 14, 1980

[54] ETHYLENE GLYCOL EXTRACTION PROCESS

[75] Inventor: David R. Bryant, South Charleston, W. Va.

[73] Assignee: Union Carbide Corporation, New York, N.Y.

[21] Appl. No.: 715,853

[22] Filed: Aug. 19, 1976

[51] Int. Cl.$^2$ ............................................. C07C 29/24
[52] U.S. Cl. ..................................... 260/450; 568/868
[58] Field of Search ............... 260/449 R, 449 L, 450, 260/637 R; 568/868

[56] References Cited

U.S. PATENT DOCUMENTS

| 2,542,454 | 2/1951 | Arnold et al. | 260/450 |
| 2,558,556 | 6/1951 | Hess et al. | 260/450 |
| 2,558,557 | 6/1951 | Hess et al. | 260/450 |
| 3,940,432 | 2/1976 | Walker et al. | 260/449 L X |
| 4,001,289 | 1/1977 | Dougherty et al. | 260/450 |

Primary Examiner—Bernard Helfin
Attorney, Agent, or Firm—Donald M. Papuga

[57] ABSTRACT

There is described a process of extracting ethylene glycol from admixture with tetraglyme containing rhodium values therein using glycerine as the extraction solvent.

6 Claims, No Drawings

ETHYLENE GLYCOL EXTRACTION PROCESS

This invention relates to a process for the recovery of ethylene glycol from admixture with tetraglyme (i.e., dimethyl ether of tetraethylene glycol). More particularly, this invention is concerned with the extraction of ethylene glycol from admixture with tetraglyme containing rhodium.

There are described in U.S. Pat. No. 3,833,634, patented Sept. 3, 1974, and U.S. patent application Ser. No. 462,109, filed Apr. 18, 1974 and now U.S. Pat. No. 3,957,857, processes for making alkane polyols, particularly ethylene glycol, by the reaction of oxides of carbon (particularly carbon monoxide) and hydrogen in the presence of a rhodium catalyst in which rhodium is in complex combination with carbon monoxide, i.e., a rhodium carbonyl complex. A preferred method for effecting that process involves forming a homogeneous liquid phase mixture of the rhodium carbonyl complex in a solvent such as tetraglyme and feeding carbon monoxide and hydrogen to the mixture. By maintaining the mixture at a temperature and pressure sufficient to effect a reaction between the carbonyl species and hydrogen in the mixture one is able to produce a mixture of ethylene glycol, glycerine, methanol, ethanol, methyl formate, and the like.

The disclosures of the patent and the application are incorporated herein by reference to establish the capability for producing a product mixture of ethylene glycol dissolved in tetraglyme which also contains the rhodium values derived from or in the form of the catalytic species. Both the patent and the application state in a general way that the products of the reaction can be recovered by distillation or extraction. However, indiscriminate distillation or extraction can cause losses of rhodium values.

In U.S. patent application Ser. No. 506,864, filed Sept. 17, 1974 and now U.S. Pat. No. 4,001,289, commonly assigned, there is described a process for separating the products of the aformentioned reaction which involves combining water and an extraction solvent with the homogeneous liquid phase mixture derived from the reaction. The products are concentrated in the resultant water phase and the rhodium values are concentrated into the extraction solvent phase.

Application Ser. No. 506,864 points to the necessity of avoiding excessive losses of rhodium values. Rhodium is a costly metal. Small losses of rhodium in carrying out this homogeneous liquid phase reaction process, either during the reaction or in the recovery of reaction products can make the process uneconomical for commercial purposes.

Though the process of Ser. No. 506,864 is superior to simple distillation alone, and defines a unique extraction process, it is not without certain disadvantages. For example, it is most difficult to keep water from being introduced into the reaction solvent. Since the extraction solvent is a liquid which is different from the components of the homogeneous liquid phase reaction mixture, it is usually necessary to separate it from the tetraglyme solvent and the rhodium values being recycled to the reaction. This last separation provides another opportunity of lose some rhodium values.

There is described herein a process for recovering products from the homogeneous liquid phase reaction mixture obtained from the aforementioned reaction which avoids the extra separation step of the process of Ser. No. 506,864 and avoids the use of extraction solvents which are alien to the components of the reaction.

The process of this invention is predicated on the discovery that glycerine has limited solubility in tetraglyme and that ethylene glycol partitions favorably to it. It has also been discovered that this partitioning effect is adversely affected by the presence of other alcohols and water. It is believed that these other components increase the solubility of glycerine in tetraglyme and vice versus, thereby increasing the amount of glycerine which is required to achieve partitioning or reducing the capability to achieve a discriminating separation of ethylene glycol. As noted above, glycerine is a product formed in the aforedefined homogeneous liquid phase reaction.

The maximum amount of glycerine that can be dissolved in tetraglyme, determined at 25° C., will form a solution containing 6.5 weight percent of glycerine. The maximum amount of tetraglyme that can be dissolved in glycerine, determined at 25° C., will form a solution containing 0.78 weight percent of tetraglyme.

The process of this invention involves separating ethylene glycol from admixture with tetraglyme containing rhodium therein. The ethylene glycol and rhodium are provided by the homogeneous liquid phase reaction, in the presence of rhodium as a carbonyl complex, of oxides of carbon (especially carbon monoxide) wherein tetraglyme is the solvent. This separation is achieved by contacting such admixture with an amount of glycerine greater than that amount which is soluble in the admixture. This causes two liquid phases to be formed. At least a portion of the ethylene glycol enters the phase richer in glycerine. The greater portion of the rhodium is contained in the phase richer in tetraglyme. The ethylene glycol is thereafter recovered from admixture with such glycerine.

The homogeneous liquid phase reaction mixture obtained from the reaction may be treated directly with glycerine according to the process of this invention. However, there are reasons for subjecting the mixture to mild distillation to drive off the low boiling components present in the mixture, such as methanol, ethanol, methyl formate, and water. It is believed, based on the evidence obtained to date, that these lower boilers repress the partitioning affinity that ethylene glycol has for the glycerine over the tetraglyme phase. Thus the process of this invention envisions a conventional distillation, preferably at atmospheric pressure or higher pressures, to distill these lower boilers from the mixture.

In particular, the experiments to date suggest that the lower boilers and higher temperatures repress extraction efficiency. Consequently, it will probably be desirable to strip the lower boilers from the mixture prior to the extraction and the extraction should be conducted at lower temperatures, e.g., room temperature.

It may be desirable to operate the extraction process under an atmosphere of carbon monoxide to help in maintaining the solubility of the rhodium values.

This extraction may be carried out in any of the conventional apparatus employed for effecting such types of extraction. Countercurrent or concurrent flow, continuous extraction procedures are believed suitably employable to practice this invention.

The following example further illustrates the practice of this invention.

EXAMPLE 1

A 150 ml. capacity stainless steel reactor capable of withstanding pressures up to 7,000 atmospheres was charged with a premix of 38 cubic centimeters (cc) of tetraglyme, 38 cc of glycerine, 3.0 millimoles (mmols), 0.77 grams, of rhodium dicarbonylacetylacetonate, and 7.0 mmols of N-methylmorpholine. The reactor was sealed and charged with a gaseous mixture, containing equal molar amounts of carbon monoxide and hydrogen, to a pressure of 8,000 pounds per square inch (psig). Heat was applied to the reactor and its contents; when the temperature of the mixture inside the reactor reached 190° C., as measured by a suitably placed thermocouple, an additional adjustment of carbon monoxide and hydrogen ($H_2$:CO=1:1 mole ratio) was made to bring the pressure back to 8000 psig. The temperature was maintained at 240° C. for 4 hours. During this period of time additional carbon monoxide and hydrogen was added whenever the pressure inside the reactor dropped below about 7500 psig. With these added repressurizations the pressure inside the reactor was maintained at 8000 psig ±400 psig over the entire 4 hour period.

After the 4 hour period, the vessel and its contents were cooled to room temperature, the excess gas vented and the reaction product mixture was removed and was found to consist of two liquid phases. Analysis of each of the two liquid phases containing reaction product was made by gas chromatographic analysis using a Hewlett Packard FM$^{TM}$ model 810 Research Chromatograph.

Rhodium recovery was determined by atomic absorption analysis of each of the liquid phases after the venting of the unreacted gases at the end of the reaction.

The following is the analysis of each layer:

|  | Top Layer | | Bottom Layer | |
| --- | --- | --- | --- | --- |
|  | gms | wt. % | gms | wt. % |
| Water | 0.48 | 1.21 | 0.93 | 2.09 |
| Methyl formate | 0.07 | 0.17 | — | — |
| Methanol | 1.01 | 2.54 | 1.21 | 2.71 |
| Ethanol | 0.08 | 0.20 | 0.08 | 0.18 |
| Ethylene glycol | 0.73 | 1.85 | 1.51 | 3.39 |
| Propylene glycol | 0.13 | 0.33 | 0.21 | 0.46 |
| Glycerine | 9.44 | 23.8 | 28.9 | 64.9 |
| Tetraglyme | 24.09 | 60.8 | 9.29 | 20.9 |
| Rh | 1530 ppm | | 50 ppm | |

What is claimed is:

1. The process of separating ethylene glycol from admixture with tetraglyme containing rhodium therein which ethylene glycol and rhodium are provided by the homogeneous liquid phase reaction in the presence of rhodium as a carbonyl complex of oxides of carbon and hydrogen wherein the tetraglyme is a solvent therefor, which comprises contacting said admixture with an amount of glycerine greater than that amount which is soluble in said admixture thereby forming two liquid phases, one which is richer in glycerine and the other containing the greater concentration of tetraglyme and causing at least a portion of said ethylene glycol to enter the phase richer in glycerine, maintaining the greater portion of the rhodium with the phase containing the greater concentration of tetraglyme, and recovering ethylene glycol from said glycerine.

2. The process of claim 1 wherein the admixture also contains methanol.

3. The process of claim 2 wherein the admixture also contains water.

4. The process of claim 2 wherein the admixture contains methyl formate.

5. The process of claim 1 wherein the extraction is conducted at a reduced temperature.

6. The process of claim 1 wherein the admixture is free of at least one of water, methanol, and methyl formate.

* * * * *